Figure 3:
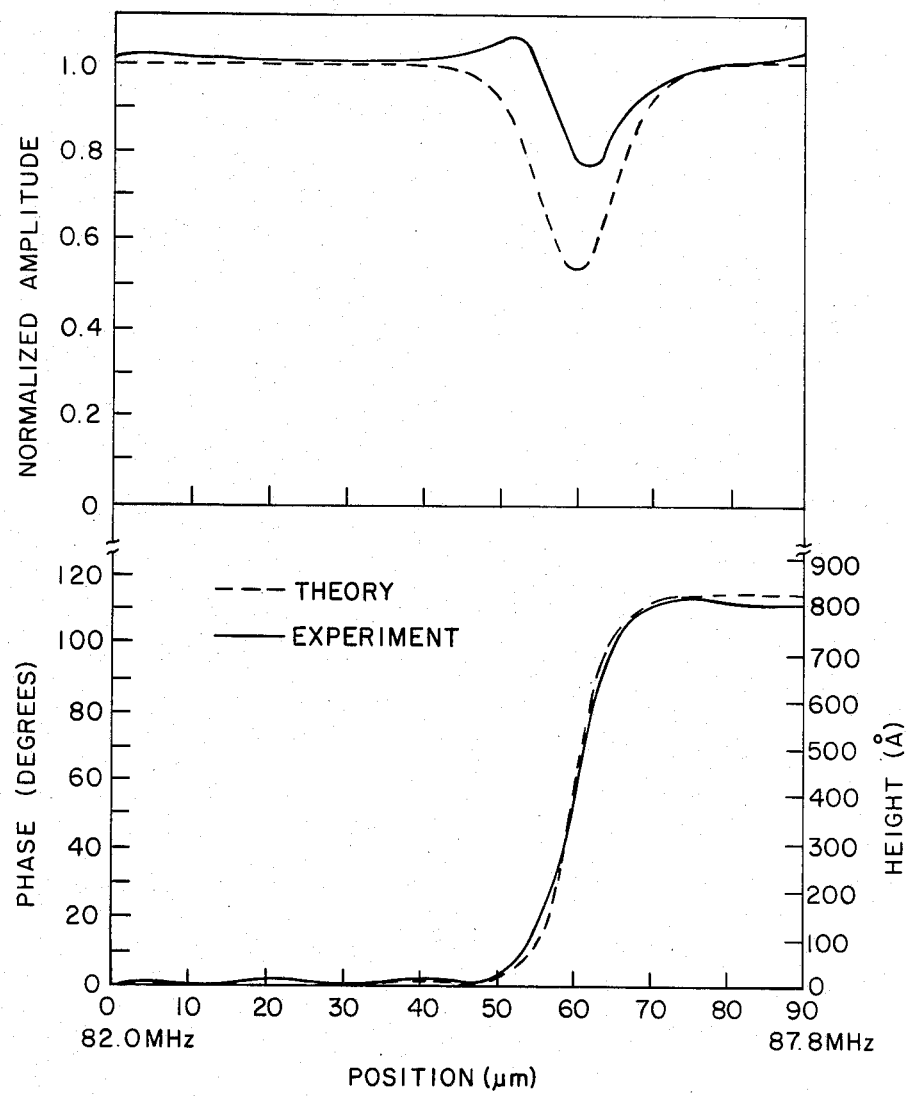

United States Patent [19]

Jungerman et al.

[11] Patent Number: 4,627,730

[45] Date of Patent: Dec. 9, 1986

[54] OPTICAL SCANNING MICROSCOPE

[75] Inventors: Roger L. Jungerman, Palo Alto; Gordon S. Kino, Stanford, both of Calif.

[73] Assignee: The Board of Trustees of the Leland Stanford Junior University, Stanford, Calif.

[21] Appl. No.: 628,181

[22] Filed: Jul. 6, 1984

[51] Int. Cl.$^4$ ............................................. G01B 9/02
[52] U.S. Cl. .................................... 356/349; 356/359
[58] Field of Search ........................ 356/349, 359, 360

[56] References Cited

U.S. PATENT DOCUMENTS 3,796,495  3/1974  Laub .................................... 356/349
4,353,650  10/1982  Sommargren .................. 356/360 X

FOREIGN PATENT DOCUMENTS 2128234  5/1984  United Kingdom .

Primary Examiner—David C. Nelms
Assistant Examiner—Matthew W. Koren
Attorney, Agent, or Firm—Flehr, Hohbach, Test, Albritton & Herbert

[57] ABSTRACT

A scanning optical microscope causes a collimated light beam to impinge on a Bragg cell. A high frequency signal applied to another surface of the Bragg cell modulates the impinging light beam. The output of the Bragg cell comprises two waves: a portion of the impinging light beam which passes directly through the cell or diffraction grating, and a second deflected output beam whose frequency is shifted by the frequency of the applied signal. By modifying the frequency of the applied frequency signal, the deflected beam may be scanned across the surface, while the reference beam remains in place and serves as a phase reference. By detecting the two beams reflected from the surface on a single photodetector, shifts in phase and amplitude of the deflected beam can be determined. To provide further isolation of the system from external vibration, a second input light beam is applied to the diffraction grating, the input of this second beam being in a plane which is essentially perpendicular to the direction of the scanned output beam. This input beam, after passing through the diffraction grating, will provide two further beams which impinge on the surface. These two beams, which are to serve as reference beams, should be focused on a known flat surface; alternatively, the size of these beams may be expanded so their size is very large relative to any surface feature to be detected; or as a further alternative, they may be reflected from a known stable reference surface. In either event, the surface reflection of these beams is detected at a separate photodetector; upon mixing with the scan beam, the reference can be used to detect any changes in phase and amplitude, while cancelling out variations due to changes in frequency of the modulating optical wave.

18 Claims, 5 Drawing Figures

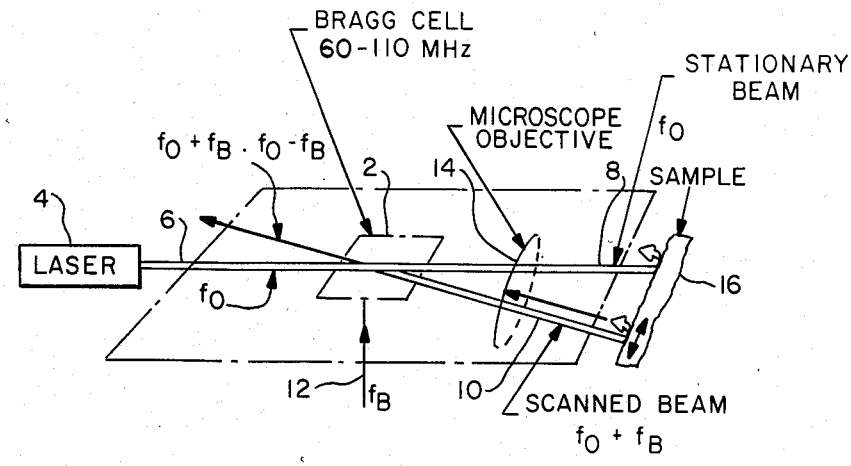
FIG.—1a
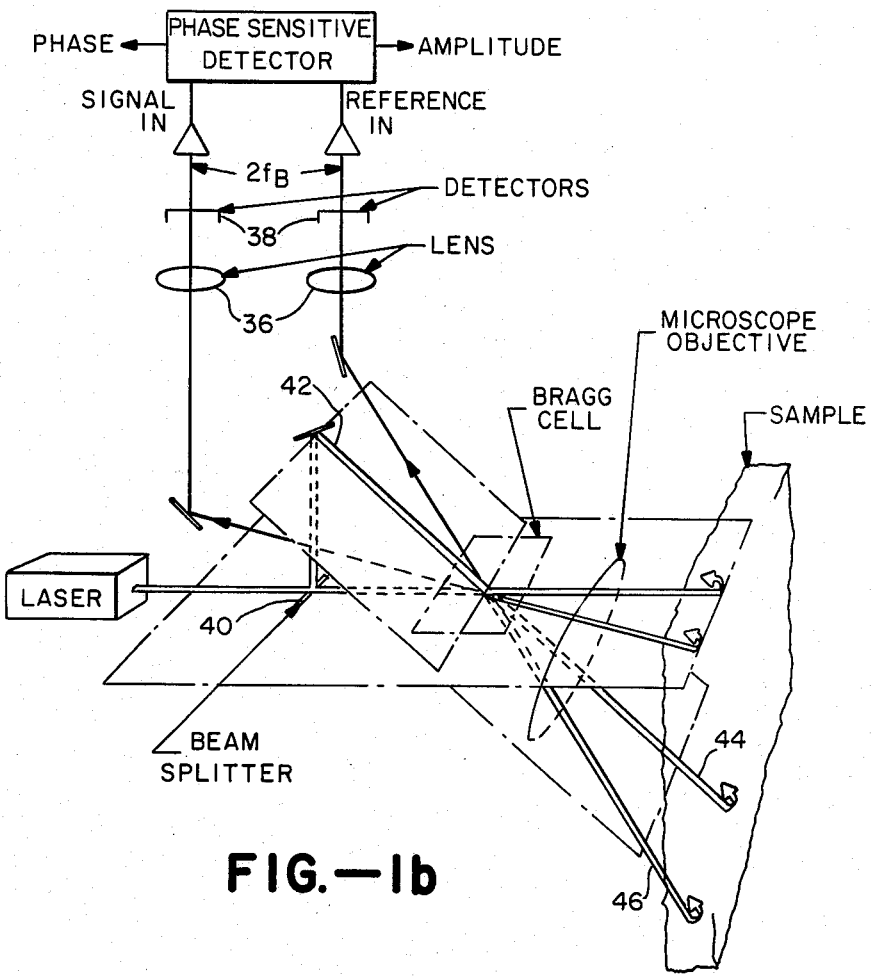
FIG.—1b

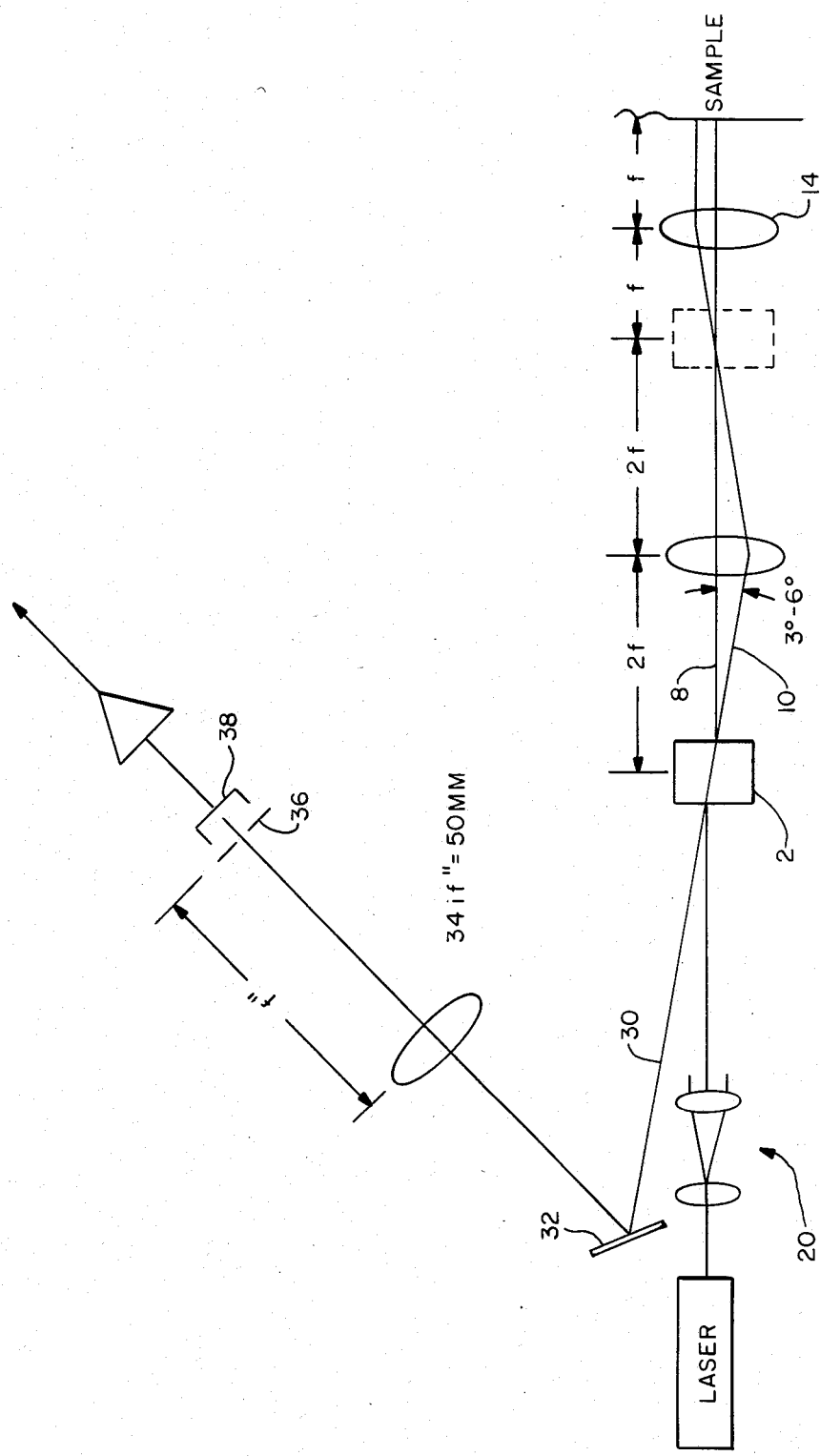
FIG.—1c

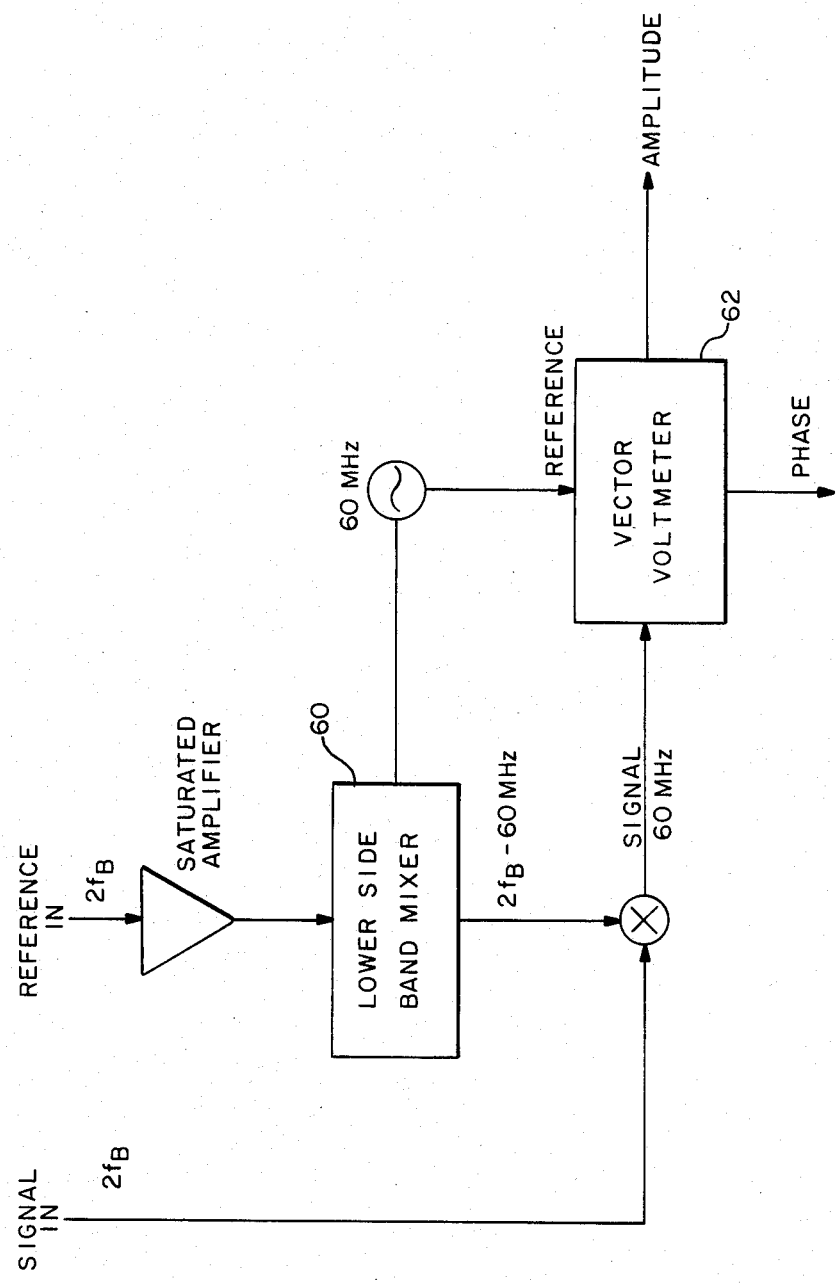
FIG.—2

OPTICAL SCANNING MICROSCOPE

The U.S. Government has rights in this invention described and claimed herein pursuant to AFOSR Contract No. F49620-49-C-0217.

This invention is directed generally to the field of optical scanning microscopes, and more particularly to a phase sensitive optical scanning microscope.

Nondestructive testing, especially in fields such as manufacture of integrated circuits is becoming extremely important as the dimensions of features in integrated circuits approach one micron or less. Such nondestructive testing would provide quantitative measurements of the surface, profiles and near surface material properties of products used in the manufacture of circuits.

This is especially important in the measurement of the thin films of metal that must be deposited on silicon chips. Ideally, both the thickness and the width of the film is examined for blemishes, foreign particles, flatness and to insure the film is properly bonded at all points to the material.

Optical microscopy has been widely used as a method of evaluating small scale surface features. However, in fields where both the lateral dimensions and the height are of interest, conventional optical microscopy gives little quantitative information. It has been suggested in the past to use differential phase contrast to provide qualitative contrast for objects differing from their surroundings in optical phase rather than amplitude. However, it is apparent that it is very difficult to extract precise height information from such images.

Interference microscopy involves the resolving of fringes to evaluate surface height; however, again the fringe maps are difficult to interpret.

It is an objective of the present invention to provide an improved optical microscope.

It is a further objective of the present invention to provide an optical microscope which can measure differences in height to a very precise degree.

More specifically, it is an objective of the present invention to measure thickness of films or the like or relative thicknesses to accuracy of less than one hundred angstroms.

In any such microscopy, it is extremely desirable to be able to scan the microscope across the surface in order to judge variations in height relative to a reference. This can be utilized both to determine the width of features, and to test the smoothness of surfaces and the success in bonding films to surfaces.

It is an objective of the present invention to present an electronically scanned optical microscope.

Earlier work done on optical profilometry using a differential technique or by heterodyning does not make use of or has not been able to successfully incorporate electronic scanning; Therefore such systems had to rely on mechanical scanning. It is an objective of the present invention to incorporate in an optical microscope means for performing the scanning of the surface of the subject electronically in order to maximize the scanning accuracy and minimize the susceptibility to vibration or mechanical shock.

These and other objectives are achieved in the present invention which comprises a scanning optical microscope in which a collimated light beam such as a laser beam impinges on an acousto-optic deflection such as a Bragg cell. An appropriate high frequency signal may be applied to an acoustic transducer on another surface of the Bragg cell to modulate the impinging light beam. The output of the Bragg cell comprises two waves: a portion of the impinging light beam which passes directly through the cell or diffraction grating, and a second deflected output beam whose frequency is shifted by the frequency of the applied signal. By modifying the frequency of the applied frequency signal the deflected beam may be scanned across the surface, while the reference beam remains in place and serves as a phase reference. By detecting the two beams reflected from the surface, on a single photodetector, shifts in phase and amplitude of the deflected beam can be determined.

In a further modification which effectively incorporates an internal reference to provide significant further isolation of the system from external vibration, a second input light beam is applied to the diffraction grating, the input of this second beam being in a plane which is essentially perpendicular to the direction of the scanned output beam. This input beam, after passing through the diffraction grating, will provide two further beams which impinge on the surface. These two beams which are to serve as reference beams, should therefore be focused on a known flat surface; alternatively, the size of these beams may be expanded so that their size is very large relative to any surface feature to be detected; or, as a further alternative they may be reflected from a known stable reference surface. In either event, the surface reflection of these beams is detected at a separate photodetector; upon mixing with the scan beam, the reference can be used to accurately detect any changes in phase and amplitude, while canceling out variations due to changes in those due to changes in frequency of the modulating optical wave in the Bragg cell.

The system of the present invention incorporates these internal references which make it largely insensitive to environmental vibrations which are a common problem in interferometers. Further, in the present invention, the information from the scan is obtained in a form which is directly compatible with digital processing. This advantage occurs because since both amplitude and phase are measured and detected; it is possible to take a Fourier transform of the complex spatial variation. This analysis system can be used with or without a Fourier transform processing to remove aberrant effects in the optical system as well as accurately determine the lateral dimensions of surface features such as line widths on integrated circuits.

On a sample of uniform composition, by use of the reference beam and deflected scanning beam, the optical phase can be easily calibrated to yield the height of surface features. By scanning the beam across the surface, the width and other dimensions of the surface features can also be accurately determined. Thus, the scanning microscope can be used as a noncontacting optical profilometer which provides height information and width information similar to that obtained using a mechanical stylus profilometer but without damage to the sample and with greatly increased accuracy. In its simplest embodiment the phase measurement provides height information and the amplitude measurement provides width information. but when the materials being measured are thick or have several layers, or the width of the feature to be measured in comparable to beam spot size the problem of measurement is much more complicated. In this case it is extremely helpful to have separate phase and amplitude information which can be processed digitally. As an example it can be difficult to measure the width of a metal strip on a fused quartz substrate, when the width of the strip is comparable to a spot size of the beam. If the beam is scanned across the strip we obtain a curve of intensity as a function of position. It is difficult to judge whether we should take the distance between half the full intensity points or use some other criterion for the width of the strip. By using amplitude and phase information; the response obtained is the convolution of the line spread function P(x) of the beam and the reflection function of the strip $\Gamma(x)$, i.e. the response is $$V(x) = \Gamma(x) * P(x)$$

where * denotes convolution, and x is the spatial position along the substrate.

The strip is of width D, the Fourier transform of $\Gamma(x)$ in the spatial domain is $$\Gamma(k) = \int_{-\infty}^{\infty} \Gamma(x) * e^{jkx} dx$$

$$= \delta(o) + \Gamma_o d \frac{\sin(kd/2)}{kd/2}$$

where $\Gamma_o$ is the amplitude and phase reflectivity of the strip and $\delta(o)$ is a Dirac delta function corresponding to the transform of the reflectivity of the substrate. We can write $$V(k) = \Gamma(k) P(k)$$

Since V(k) the spatial frequency response of the system is a product of the spatial frequency responses of the lens and the substrate, we can search for the zeros of the response of $\Gamma(k)$ and from their spacing determine D. The result should be independent of P(k) provided P(k) is finite for $|k|$ larger than values of K for which $\Gamma(k) = 0$. Thus digital processing of the input signal can be very important for determining the width of substrate features, and for removing lens aberrations.

The features and advantages of the present invention, as well as a embodiment thereof, will become more apparent with the study of the following figures in conjunction with the following description of the preferred embodiment, wherein FIGS. 1A and 1B illustrate the utilization of a Bragg cell to apply the optical beams to the sample of interest;

FIG. 2 is a block diagram of the elements necessary to analyze the reflected optical scanning beam; and FIG. 3 is a graph showing results of an actual experiment conducted using the embodiment of FIGS. 1 and 2.

The basic system as shown in FIG. 1A of the present invention utilizes a Bragg cell 2 such as already well known in the field of optics on which an output beam from a laser 4 or other source of highly collimated light impinges. As a result of the impingement of the beam 6, at a frequency $f_0$, the output of the Bragg cell consists of two beams. One beam 8 comprises a portion of the impinging beam at the same frequency $f_0$ passing directly through the Bragg cell. The other beam, which is to be the scanned beam 10 passes out of the Bragg cell at a frequency $f_0$ plus $f_B$. The frequency $f_B$ is the frequency of an input signal 12 which is applied to an adjacent face of the Bragg cell through a transducer to set up an acoustic wave through the Bragg cell which interacts with the impinging collimated light beam.

The Bragg cell 2 thus effectively acts as a diffraction grating, passing a portion of the beam through unimpeded, and a second portion at a shifted frequency. The two beams are focused by a microscope objective lens 14 on the sample 16, the sample being located at the focal point of the objective lens. In a preferred embodiment of the present invention shown in FIG. 1C, the laser 4 is a single frequency argon ion laser with etalon whose output is applied to a beam expander 20. The purpose of the beam expander is to provide an expanded beam of light; when the light passes through a microscope objective lens, the broad beam of light can be focused to an extremely small point by the objective lens. The reason for focusing a broad beam of light to a single point is to get the highest possible spatial resolution, which is especially important in examination of integrated circuits and the like.

The beam of light is next passed through a $TeO_2$ Bragg cell 12. This Bragg cell has a 60 to 110 Mhz swept frequency applied to a transducer attached to the edge of the cell from a voltage controlled oscillator. The light passing out of the Bragg cell as previously discussed is split into two beams 10, 8 with half of the light in each beam. As discussed above, the idea is to focus the light onto the sample through a microscope objective lens in two spots which are as small as possible. To analyze the information accurately, it is necessary to have the Bragg cell at the back focal plane of the microscope objective lens. However, because of the short focal length of the microscope objective lens 14, the back focal plane is actually within the mounting hardware of the microscope objective lens. Therefore, a field lens 24 is provided for refocusing the two beams 8, 10 so that the Bragg cell image which is shown in dotted lines in the schematic diagram actually does appear to be at the back focal plane of the microscope objective lens as is apparent from the diagram, the sample is placed at the front focal plane of the same microscope objective lens. The distance f' is a value which depends on the numerical aperture which is in turn is defined by how steeply the light approaches the lens.

The reflections of the two light beams travel back toward the Bragg cell along the same path as they followed in traveling toward the sample. Thus when the scan beam 10 returns to the Bragg cell, it is again split in half, with half of the reflected signal going back toward the laser, and the other half traveling the analysis path 30. In addition, half of the stationary beam 8 is reflected out of the Bragg cell at the Bragg angle along the detection path 30. These beams which now have components $f_0 + f_B$ and $f_0 - f_B$ respectively strike the mirror 32 and passes through a lens 34 and photo detector 38 to the detection electronics. A pin hole 36 can be placed in front of the detector as a spatial filter. The output of the photodetection is at a frequency $f_0 + f_B - (f_0 - f_B) = 2f_B$.

In order to provide a stable reference which indicates the frequency and phase of the swept frequency in the Bragg cell, it would be thought obvious to simply apply the 2nd harmonic of the signal frequency $2f_B$ to the detector electronics and use it as a phase reference. In fact, due to delays which occur in the acoustic signal as it passes across the Bragg cell, such a system would not provide sufficient phase accuracy. Therefore a further pair of reference beams are provided by applying a second laser beam of fixed frequency to the Bragg cell. Ideally, as shown in FIG. 1B, in order that this second beam has exactly the same frequency and phase characteristics as the laser beam which provides the scanned beam 10, beam splitter 40 is utilized to provide a second beam 42, which in turn is separated into two components. One half of the beam passes directly out of the Bragg cell along the path 44, the other half leaves the Bragg cell along a Bragg angle path 46. Both of these beams are imaged on the sample 16 exactly as described above for the first laser beam through the microscope objective lens 14. These beams are reflected back, and combined and applied through a lens and detector to the phase sensitive detector electronics.

It is important to note a second advantage of this particular invention resides in the use of coherent detection by mixing of two beams at the photo sensor of the present invention. Specifically, the use of this type of detector provides a type II confocal point microscope (see G. S. Kino, *Scanned Image Microscopy*, E. A. Ash, Ed., Academic Press, London, Page 1, (1980)) which is scanned electronically across a surface. Such electronic scanning of a pin-point confocal microscope beam has never been previously achieved. Such scanning usually has been achieved in the prior art only by mechanical means. The photodiode detector is placed at the focus of a lens to compensate for the variation of the Bragg angle with frequency. FIG. 2 shows the signal processing used to detect the amplitude and phase of the optically derived signals at $2f_B$. Since it is advantageous to detect phase at a fixed frequency, the reference signal is first limited and then single sideband modulated at an intermediate frequency of 60 MHz. Mixing this reference with the signal photodetector output gives a fixed frequency signal at 60 MHz which contains all the amplitude and phase information.

In this configuration, the Rayleigh resolution is equal to that of the incoherent microscope, while the 3 dB resolution is somewhat better, and the ripples observed while scanning across a discontinuity are reduced over that of a partially incoherent Type I system. Specifically, the reference beams 44,46 are mixed in the photodiode to give a signal at $2f_B$; the $2f_B$ signal is single side band mixed with a 60 megahertz signal in a mixer 60; The reference beam and the actual scan signal beam are differenced; the combined signals are analyzed in a vector voltmeter 62 for the change in amplitude and change in phase information which reflects the changes in height and the width in such changes in the system. This information is available because the phase of the signal at $2f_B$ depends on the optical path length difference between the two beams 8, 10 impinging on the sample 16, since the optical signals at frequencies $f_0+f_B$ and $f_0-f_B$ originate from the scan and stationery spots on the sample respectively. The theory on which this analysis is based is that for plane wave illumination, a surface height variation of h will introduce an optical phase change of 2kh as the beam is scanned over a feature of height h. For a tightly focused beam, the observed phase change is less since much of the incident light arrives at the sample at off-normal incidence. By integrating over a uniformly illuminated spherical lens aperture, it can be shown that the feature introduces a phase change of $$\Delta\phi = kh(1+\cos\theta_0) \qquad (1)$$

where $\theta_0$ is the half angle of the objective aperture. As $\theta_0$ approaches zero, this formula reduces to the phase change for a plane wave. Changes in the distance from the lens to the sample do not affect the measurement since only path length differences between the two beams are important. Thus, mechanical vibrations in the lens spacing do not disturb the measurements so long as they are less than the depth of focus of the objective. In the simplest configuration (FIG. 1a), the measurement is sensitive to surface tilt; in the more sophisticated example of FIG. 1B, sensitivity to tilt is eliminated.

To measure the phase shift in the interference signal at $2f_B$ as the Bragg cell frequency $f_B$ is varied over the scan range, an electronic reference signal is required. Simply frequency doubling the Bragg cell drive signal is not sufficient since the finite acoustic delay in the Bragg cell will produce a large linear phase shift as the Bragg frequency is changed. Instead, a second optical signal is generated (FIG. 1b) by splitting the beam incident on the Bragg cell in a direction perpendicular to the direction of acoustic wave propagation. Thus, four spots are focused on the sample. If the sample geometry is chosen so that the second set of spots is located on a uniform flat section of the sample, then they can be used for a reference. Alternatively, the second set of spots can be magnified to be much larger than the size of surface features of interest and placed anywhere on the sample, or reflected to a flat reference surface off the sample.

EXAMPLE I

Calibration scans are performed on an optical flat and amplitude and phase variations due to the electronics as well as optical aberrations are divided out and subtracted out, respectively. After this calibration, scans across a flat uniform sample show amplitude variations less than 3% and phase variations of less than 5°, suggesting a minimum surface height sensitivity of better than 50 A°.

In an experiment, 5 mW from an etalon controlled single-frequency argon-ion laser at 510 nm was used. The $TeO_2$ Bragg cell has a bandwidth of 60–110 MHz and deflection angles of 3° to 6°. Microscope objectives with numerical apertures in the range of 0.1 to 0.86 were used. The length of the scan on the sample is proportional to the frequency change times the objective focal length. With the higher numerical aperture, a $1/e^2$ spot radius of 1 $\mu$m was measured by examining the reflection from a metallized edge.

FIG. 3 demonstrates an initial experiment on the application of the microscope to optical profilometry. In order to check the system performance, our aim was to eliminate phase changes due to the use of a wide aperture lens caused by polarization effects and changes in phase of the reflection coefficient. A step of aluminum 900 Å thick (as measured with a mechanical stylus) was deposited on a glass substrate metallized with 500 Å of aluminum. To simulate plane wave illumination, a long focal length microscope objective (16 mm focal length) was illuminated with a narrow beam less than 1 mm in diameter. This yields an effective numerical aperture of less than 0.03. The Bragg cell frequency was scanned over the range of 82.0 MHz to 87.8 MHz, causing the focused beam to scan across 90 $\mu$m on the sample. In FIG. 3, the amplitude and phase of the scanned spot are shown. After calibration, 5° of phase offset has been subtracted from the experimental phase curve. The theoretical curves are evaluated numerically for a Gaussian beam with a $1/e^2$ radius of 9 $\mu$m, which in consistent with the small numerical aperture of the lens used. The beam is assumed to have constant optical phase and is convolved across the phase step. Due to aberrations and misfocusing, there may be phase variations across the beam which could account for the discrepancy between the experimental and theoretical amplitude curves.

The phase curve indicates a step height of 820 Å, which is in fair agreement with the mechanical stylus measurement of 900 Å, and demonstrates the ability to obtain good quantitative contrast on samples with features differing only in optical phase.

In summary, The present invention provides an electronically-scanned optical microscope which can quantitatively measure amplitude and phase. Surface height variations can be accurately measured with the system. In addition, the ability to measure optical phase promises to make possible digital filtering to remove the the effect of aberrations and to accurately determine lateral dimensions on the sample.

Modifications to the disclosed preferred embodiment may become apparent to one of skill in the art who studies the subject invention disclosure. Therefore the scope of the present invention shall be limited only by the following claims.

What is claimed is:

1. An optical scanning microscope comprising means for focusing at least two optical beams on a sample under study, means for optically scanning one of said beams across the surface of the sample independent of movement of the sample itself, the other of said optical beams being held stationary relative to a fixed point on the surface of the sample whereby the distance between the landing points of said beams over the surface of the sample is variable, means for comparing the phase of the reflected beams to determine the phase shift of the scanned beam relative to the phase of the stationary beam as representing surface variation anywhere on the surface of the object covered by said scanned beam.

2. An optical scanning microscope as claimed in claim 1 wherein said focussing means comprises a Bragg cell responsive to an optical input beam.

3. An optical scanning microscope as claimed in claim 2 including means for supplying an input beam of collimated light comprising a laser.

4. An optical scanning microscope as claimed in claim 1 wherein said focussing means comprises a diffraction grating for splitting a collimated input beam of light into said two output beams comprising an undiffracted beam and a diffracted beam.

5. An optical scanning microscope as claimed in claim 4 wherein said input beam has a given frequency $\omega_O$, said scanning means comprising frequency shifting means for modifying the frequency of one of said output beams to a frequency $\omega_O + \omega_B$, $\omega_B$ being the acoustic output frequency of said scanning means.

6. An optical scanning microscope as claimed in claim 5 wherein said focussing means comprises a Bragg cell, said scanning means including means for supplying an acoustic wave of frequency $\omega_B$ to said Bragg cell.

7. An optical scanning microscope as claimed in claim 6 comprising a microscope objective lens between said Bragg cell and said sample for focussing the output beams on the sample.

8. An optical scanning microscope as claimed in claim 1 wherein said comparing means comprise a photodetector means for receiving said reflected wave, and means coupled to the output of said photodetector for determining phase shift of the scanned beam relative to the reference, stationary spot on the sample.

9. An optical scanning microscope as claimed in claim 8 wherein said reflected beams return to said focussing means, and including means for focussing said reflected beams on said photodetector during scanning of said beams.

10. An optical scanning microscope as claimed in claim 9 including means providing a pinhole opening for focussing said reflected rays on said photodetector.

11. An optical scanning microscope as claimed in claim 1 further comprising means for supplying first and second input beams to said focusing means, said focusing means being responsive thereto to focus two additional optical beams on a reference region of the sample under study.

12. An optical scanning microscope as claimed in claim 3 further comprising means for supplying a second input beam to said Bragg cell, said Bragg cell being responsive thereto to focus two additional optical beams on a reference area of said sample.

13. An optical scanning microscope as claimed in claim 12 wherein said second input beam lies in a plane perpendicular to the direction of scanning of said scanned output beam.

14. An optical scanning microscope as claimed in claim 13 further comprising means for magnifying said two additional optical beams to a size larger than the sample area of interest.

15. An optical scanning microscope as claimed in claim 11 comprising means for comparing the reflected phase of said scanned beam with the phase of said reference beams.

16. An optical scanning microscope as claimed in claim 13 comprising means for comparing said first reflected scanned signal beam and said reference area signal beam to determine phase shift in said reflected scanned signal.

17. An optical scanning microscope as claimed in claim 16 including means for mixing said reflected reference signal beam with a substantially higher intermediate signal frequency, means for combining said mixed signal with said first reflected scanned signal beam, and said comparing means responding to said combining means to develop said phase information.

18. An optical scanning microscope as claimed in claim 17 wherein said comparing means further comprise means responsive to said combining means to develop a signal indicating changes in amplitude in said scanned signal.

* * * * *